US00PP31786P2

(12) United States Plant Patent
Traven et al.

(10) Patent No.: US PP31,786 P2
(45) Date of Patent: May 19, 2020

(54) ***LAVANDULA* PLANT NAMED 'TESSERACT'**

(50) Latin Name: ***Lavandula* x *intermedia***
Varietal Denomination: Tesseract

(71) Applicants: Lloyd R. Traven, Kintnersville, PA (US); Richard Grazzini, Bellefonte, PA (US)

(72) Inventors: Lloyd R. Traven, Kintnersville, PA (US); Richard Grazzini, Bellefonte, PA (US)

(73) Assignee: B&S PLANTS, LLC, Kintnersville, PA (US)

( * ) Notice: Subject to any disclaimer, the term of this patent is extended or adjusted under 35 U.S.C. 154(b) by 0 days.

(21) Appl. No.: 16/602,029

(22) Filed: Jul. 23, 2019

(51) Int. Cl.
*A01H 5/02* (2018.01)
*A01H 6/50* (2018.01)

(52) U.S. Cl.
USPC ..... Plt./445
CPC ..... *A01H 6/50* (2018.05)

(58) Field of Classification Search
USPC ..... Plt./445
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Lavandula* x *intermedia* plant named 'Tesseract' that is characterized by its foliage that is very broad and bright silver with a very thick substance, its very compact and strongly upright plant habit, its flowering stems that are strong and held upright and straight making it ideal for fresh or dry cut flowers, its large flowers on very densely flowered flower spikes, its flower petals that are a bright and deeply saturated purple color, its flower stems that are very thick and branched resulting in rebloom for a longer blooming season, its tolerance to leaf spotting and root disease, and its strong, pleasant lavender fragrance.

2 Drawing Sheets

Botanical classification: *Lavandula* x *intermedia.*
Variety denomination: 'Tesseract'.

BACKGROUND OF THE INVENTION

The present invention relates to a new and distinct cultivar of *Lavandula* x *intermedia* and will be referred to hereafter by its cultivar name, 'Tesseract'. 'Tesseract' is a new variety of English lavender suitable for landscape and container use.

The Inventors discovered the new cultivar in February of 2015 as a naturally occurring branch mutation of *Lavandula* x *intermedia* 'Niko' (U.S. Plant Pat. No. 24,193) that was growing in a greenhouse in Bellfonte, Pa.

Asexual propagation of the new cultivar was first accomplished by stem tip cuttings by one of the Inventors in October of 2016 in Bellfonte, Pa. Asexual propagation by stem tip cuttings has shown that the characteristics of the new cultivar are stable and are reproduced true to type in successive generations.

SUMMARY OF THE INVENTION

The following traits have been repeatedly observed and represent the characteristics of the new lavender. These attributes in combination distinguish 'Tesseract' as a unique cultivar of *Lavandula.*

1. 'Tesseract' exhibits foliage that is very broad and bright silver with a very thick substance.
2. 'Tesseract' exhibits a very compact and strongly upright plant habit.
3. 'Tesseract' exhibits flowering stems that are strong and held upright and straight making it ideal for fresh or dry cut flowers.

4. 'Tesseract' exhibits larger flowers on very densely flowered flower spikes.
5. 'Tesseract' exhibits flower petals that are a bright and deeply saturated purple color.
6. 'Tesseract' exhibits flower stems that are very thick and branched resulting in rebloom for a longer blooming season.
7. 'Tesseract' exhibits a tolerance to leaf spotting and root disease.
8. 'Tesseract' exhibits a strong, pleasant lavender fragrance that is floral rather than pungent.

The parent plant of 'Tesseract', 'Niko', differs from 'Tesseract' in having a taller plant height, leaves that are thinner and softer, flower stems that are weaker and thinner, thinner inflorescences and flowers that are lighter in color, more separated on the stem with a different fragrance that is sharper. 'Tesseract' can be compared to *Lavandula* x *intermedia* cultivars 'Grosso' (not patented) and 'Lavandin de Provence' (not patented). Both cultivars are similar to 'Tesseract' in having flowers that are purple in color. 'Grosso' differs from 'Tesseract' in having thinner leaves, weaker flower stems, less flowers that are lighter in color in whorls that are more separated, less winter hardiness, a more variable growth habit, and susceptibility to root rot and leaf disease. 'Lavandin de Provence' differs from 'Tesseract' in having thinner leaves that are subject to browning, weaker flower stems and growth habit, less flowers that are lighter in color in whorls that are more separated and less cold hardiness.

BRIEF DESCRIPTION OF THE DRAWINGS

The accompanying colored photographs illustrates the overall appearance and distinct characteristics of the new cultivar. The photographs were taken of plants about 8 months in age as grown outdoors in 1-gallon containers in Kintnersville, Pa.

The photograph in FIG. 1 provides a side view of 'Tesseract' in bloom.

Figure 1:
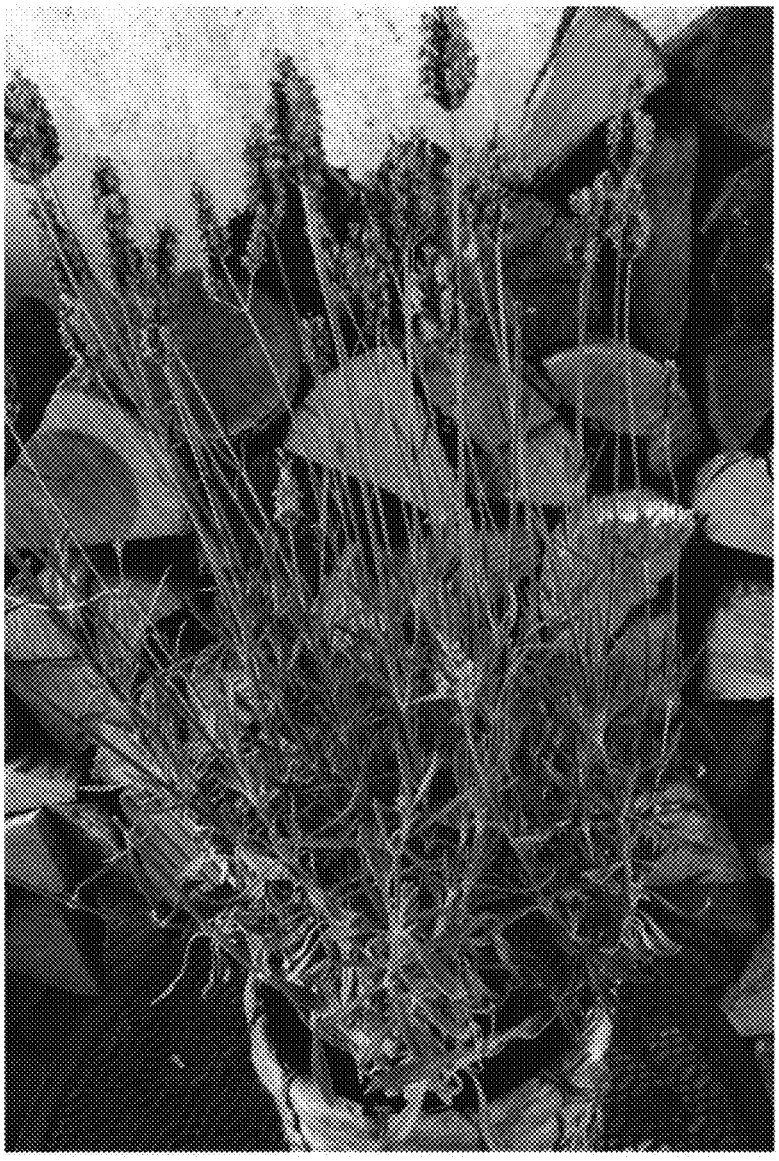
Figure 2:
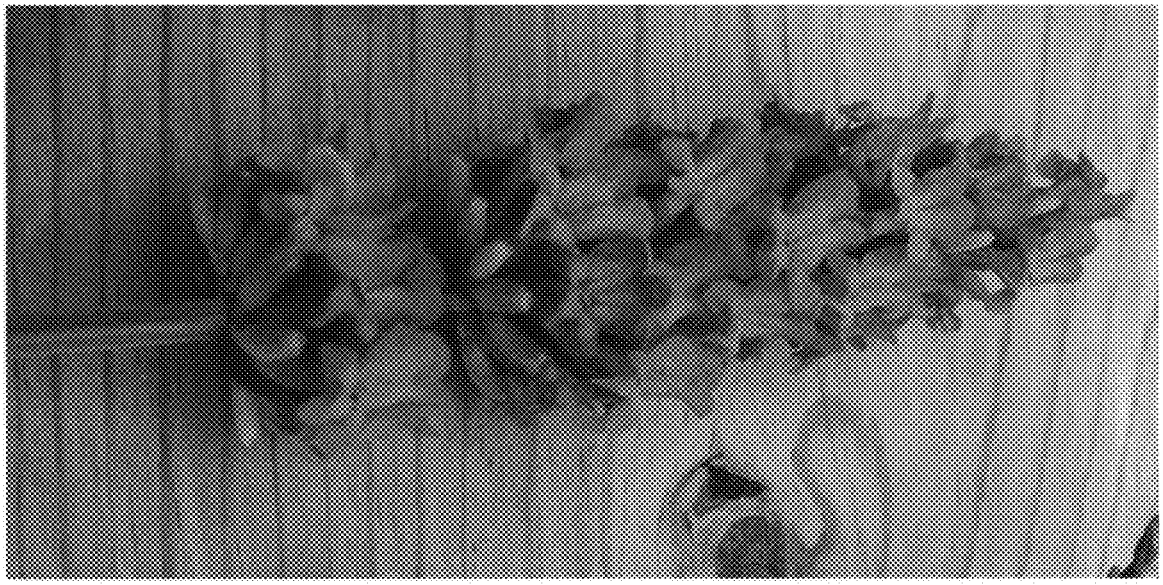

The photograph in FIG. 2 provides a close-up view of an inflorescence of 'Tesseract'.

Figure 3:
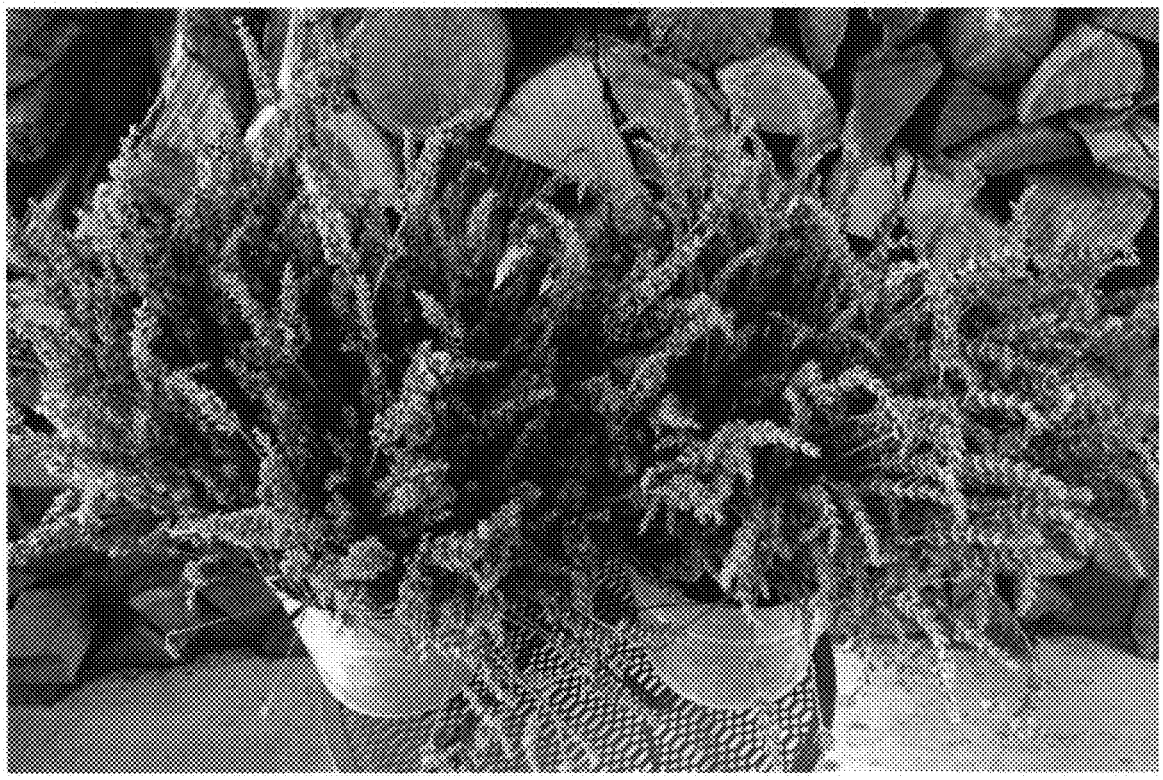

The photograph in FIG. 3 provides a view of cut flower stems of 'Tesseract' (on the left) compared to cut stems of its parent plant, 'Niko' (on the right).

The colors in the photographs are as close as possible with the photographic and printing technology utilized. The color values cited in the detailed botanical description accurately describe the colors of the new *Lavandula*.

DETAILED BOTANICAL DESCRIPTION

The following is a detailed description of 8-month old plants of the new cultivar as grown outdoors in 1-gallon containers in Bellfonte, Pa. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming habit*.—Blooms early to mid-June, continuously for 6 to 8 weeks, longer if side florets develop.

*Plant type*.—Herbaceous perennial.

*Plant habit*.—Upright with upright lateral branches.

*Height and spread*.—Reaches about 45 cm in height (including inflorescence), 29 cm in height (excluding inflorescence) and 33 cm in spread as grown in a one-gallon container, mature plant in the landscape reaches 60 cm in height (including inflorescence), 36 cm in height (excluding inflorescence) and 60 cm in spread.

*Cold hardiness*.—At least to U.S.D.A. Zone 5.

*Diseases and pests*.—Has shown good resistance to leaf spot and root disease caused by *Phytophthora* sp., *Pythium* sp. and *Rhizoctonia* sp.

*Root description*.—Fibrous, 159C in color.

*Root development*.—Roots initiate in 3 to 4 weeks, average time to produce young plant from rooted cutting is 8 to 10 weeks.

*Propagation*.—Stem tip cuttings.

*Growth*.—Moderate.

Stem description:

*Stem shape*.—Quadangular.

*Stem color*.—Young; ranging between 145A and 147A, mature wood; 165A.

*Stem surface*.—Young stems; dull and densely covered with tiny soft tomentose hairs, mature wood is slightly glossy and smooth.

*Stem size*.—Average of 25 cm in length and 4 mm in diameter.

*Stem strength*.—Strong.

*Stem aspect*.—Held upright to bowing outward.

*Branching*.—An average of 11 lateral branches on a plant developed in an 17-cm container, 1 to 2 secondary branches develop for rebloom.

Foliage description:

*Leaf shape*.—Narrowly oblong to narrowly oblanceolate to moderately revolute.

*Leaf division*.—Simple.

*Leaf base*.—Cuneate.

*Leaf apex*.—Rounded-acute.

*Leaf venation*.—Pinnate, veins match surface color.

*Leaf margins*.—Entire.

*Leaf arrangement*.—Opposite to slightly whorled.

*Leaf attachment*.—Sessile.

*Leaf number*.—Average of 50 per stem length of 25 cm.

*Leaf surface*.—Upper surface and lower surface; densely covered with tiny tomentose pubescence, too small to measure color and size.

*Leaf size*.—Average of 7 cm in length and 1 cm in width.

*Leaf internode length*.—Densely covered with foliage, ranges between 0.5 mm to 2 cm.

*Leaf color*.—Young upper and lower surface; 189A, mature upper and lower surface; NN137A.

*Leaf fragrance*.—Very strong Lavender fragrance.

Inflorescence description:

*Inflorescence type*.—Terminal verticillasters.

*Inflorescence number*.—1 per lateral stem with 1 to 3 subsequent blooms on secondary branches.

*Inflorescence fragrance*.—Pleasant strong Lavender fragrance, floral rather than pungent.

*Lastingness of inflorescence*.—Average of 12 weeks on the plant and as a fresh cut flower.

*Inflorescence size*.—Average of 11 cm in (height) and 1.5 cm in width.

*Flowers*.—Outward aspect, self-cleaning, salverform in shape, with one upper lip (split into two identical lobes), lower lip (split into three identical lobes), average total of 50 flowers and buds per inflorescence, about 7 mm in depth (height) and 5 mm in diameter.

*Flower buds*.—Average of 6 mm in length and 2 mm in diameter, elliptic to oblong in shape, color is 144C, entire surface is densely covered with tiny tomentose pubescence, too small to be measured and closest to NN155D in color and slightly translucent and matching surface color.

*Petals*.—Dull and smooth on upper and lower surfaces, rotate in arrangement, 2 (upper lip split in 2 lobes, lower lip split in 3 lobes; all lobes are identical in shape and colour), spathulate in shape, lower 50% of petals are fused into tube, entire margin, upper part of petal apex split into two lobes, lower petal apex split into three lobes, apexes are rounded, upper lip is 4 mm in length and 5 mm in width, lower lip 2 mm in length and 7 mm in width, color; upper and lower surface of petal when opening and fully open; 76A, surfaces fading to 90A.

*Sepals*.—Linear in shape, bluntly acute apex, cuneate base, color of both surfaces 147A, both surfaces are dull and densely covered with tiny tomentose pubescence.

*Calyx*.—Closed campanulate in shape, 5 mm in length and 2 mm in diameter.

*Peduncles*.—Strong, quadrangular shape, ribbed surface, average of 25 cm in length and 2 mm in diameter, growing in a vertical angle to outwardly upright, color is between 143A and 194A and densely covered with tiny tomentose pubescence.

*Pedicels*.—None present, flower attachment sessile.

*Bracts*.—Deltoid in shape and fused into tube, entire margin, acuminate apex, cuneate base, 6 mm in length and 4 mm in width, upper and lower surface colors; base 145A, mid-section to tip 146A, veins 141A, upper surface glossy and glabrous, lower surface densely covered with tiny tomentose pubescence.

Reproductive organs:

*Pistils*.—1, pistil is 5 mm in length, stigma is narrow and linear in shape, 1 mm in length, 0.5 mm in diameter and 90B in color, style is 4 mm in length and NN155D in color, ovary is 1 mm in length and diameter, round in shape and 149A in color.

*Stamens*.—4, anthers are dorsifixed, kidney-shaped, about 0.5 mm in length and 203B in color, the filament is 3 mm in length and 0.5 mm in diameter, N155D in color, pollen is abundant in quantity and N25A in color.

*Fruit and seeds*.—No fruit or seed development has been observed.

It is claimed:

1. A new and distinct cultivar of *Lavandula* x *intermedia* plant named 'Tesseract' as herein illustrated and described.

* * * * *